United States Patent [19]
Boche

[11] Patent Number: 6,096,058
[45] Date of Patent: Aug. 1, 2000

[54] SURGICAL INSTRUMENT WITH AN APPARATUS FOR LIMITING THE TRANSFER OF A FORCE

[75] Inventor: Hartmut Boche, Immenstaad, Germany

[73] Assignee: Karl Storz GmbH & Co. KG, Germany

[21] Appl. No.: 09/273,856

[22] Filed: Mar. 22, 1999

Related U.S. Application Data

[63] Continuation of application No. PCT/EP98/04577, Jul. 21, 1998.

[51] Int. Cl.⁷ ................................................ A61B 17/00
[52] U.S. Cl. ........................... 606/205; 606/174; 600/564
[58] Field of Search ............................. 606/174, 205–210; 600/564

[56] References Cited

U.S. PATENT DOCUMENTS

5,368,606  11/1994  Marlow et al. .................. 606/174
5,947,996   9/1999  Logerman ........................ 606/174

*Primary Examiner*—Michael Buiz
*Assistant Examiner*—William W. Lewis
*Attorney, Agent, or Firm*—St.Onge Steward Johnston & Reens LLC

[57] ABSTRACT

An surgical instrument comprises a movable actuation element, at least one working part moved by said actuation element, an apparatus for limiting a transfer of a force transferred via said actuation element to said at least one working part. Said apparatus has at least one wedge surface associated to said actuation element, said wedge surface rising perpendicular to its movement when moving said actuation element. A housing is provided which can be spread apart by said wedge surface by movement thereof, and an elastically spreadable ring circumferentially surrounds said housing in its spreading section, said elastically spreadable ring can close said spread housing when said wedge surface is moved out of its spreading engagement with said housing.

24 Claims, 5 Drawing Sheets

SURGICAL INSTRUMENT WITH AN APPARATUS FOR LIMITING THE TRANSFER OF A FORCE

This is a continuation of pending international application PCT/EP98/04577 filed on Jul. 21, 1998, which designated the United States.

BACKGROUND OF THE INVENTION

1. Field of the Invention

The present invention relates to an apparatus for limiting the transfer of force to surgical instruments.

The invention further concerns surgical instruments which are equipped with an apparatus of this kind.

Surgical instruments of this kind may be grasping, holding, and dissection forceps, scissors, or other instruments in which working part, usually mouth parts, are moved by manual force via an actuation element that can be moved back and forth.

2. Related Prior Art

Grasping, holding, and dissection forceps are known, for example, from the catalog "Endoskopische Chirurgie [Endoscopic surgery], 2nd edition, 1/94, section 4, Präparier- und Faβzangen [Dissection and grasping forceps]" of Karl Storz GmbH & Co., Tuttlingen, Germany.

These known forceps have an elongated cylindrical shaft at whose distal end at least two mouth parts are arranged. Arranged at the proximal end of the shaft is a handle which has the form of two scissor-like handle elements. One of the handle elements is immovably joined to the shaft, and the other, called the movable handle element, is joined via a hinge to the immovable handle element. A mechanism which serves to open and close the mouth parts has a rod-shaped actuation element, passing through the shaft, which is joined at the distal end to the mouth parts. At the proximal end, the actuation element extends out beyond the end of the stationary handle element and is joined in articulated fashion, usually via a ball-and-socket joint, to the upper outer end of the movable handle element. Pivoting of the movable handle element about the hinge axis relative to the stationary handle element causes a linear back-and-forth displacement of the actuation element in the shaft. This linear or axial back-and-forth movement is converted into a pivoting movement of the mouth parts.

Forceps of this kind are utilized in the commonly-used practice of minimally invasive surgery. In this context, the forceps are introduced into the body through trocars.

Because of the miniaturization of the mouth parts necessary for minimally invasive surgery, they are sensitive to loads, since for given hand forces the sustainable forces become smaller due to miniaturization. This also applies to dynamic devices of normal size if the design load is exceeded. The movable handle element is configured as a lever, the lever axis being represented by the hinge axis at which the movable handle element is articulated onto the other handle element. The distance from the hinge axis to the point at which the movable handle element is connected to the actuation element that is to be displaced is much shorter than the distance from the hinge axis to the finger loop arranged at the outer end of the handle element. The ratio is approximately 10:1, i.e. the closing force of a hand, approximately 10 kp, is amplified tenfold by the lever effect, i.e. to approximately 100 kp. A limitation of force is not present with the embodied kinematics of the known forceps.

In the practical utilization of surgical grasping and holding forceps, is has been found that during handling an attempt is made to clamp the object being held, for example a spherical sponge or a needle, as firmly as possible in the grasping forceps. In the case of cutting and in particular cut-through mouth parts there may be a risk, if instead of an easily cut soft tissue element a piece of cartilage or bone ends up between the mouth points, that the operator will exert a closing force which exceeds the force that can be safely sustained by the mouth parts. Strong persons can exert a closing force of 15 kp or more, which is then amplified tenfold by the lever. If overloading due to the exertion of excessive hand force, and thus high loading of the mouth parts, occurs frequently, this can cause material fatigue in the mouth part region and even breakage of the mouth parts. There exists in this context the risk that the aforesaid breakage of the mouth parts due to overloading might occur during the operation. This can result in uncontrolled damage to tissue and organs in the operative area.

DE 38 19 123 A1 discloses a surgical instrument that is equipped with an overload protector. The overload protector comprises a force reservoir which absorbs the increased tension. In the simplest case, the force reservoir comprises a helical spring.

DE 41 31 176 A1 discloses a medical instrument in which, in an overload situation, spreading of an element of the actuation rod results in positive engagement into a stationary portion of the forceps housing, e.g. by way of an elastic tubular piece.

DE 94 07 081 U1 discloses an overload protection system for motor-driven surgical instruments which can be configured as a claw coupling, friction coupling, magnetic coupling, or defined break point.

Against this background, it is the object of the present invention to create an apparatus with which overloads on the working parts of a surgical instrument can be reliably prevented.

SUMMARY OF THE INVENTION

According to the present invention, the object is achieved by an apparatus for limiting the transfer of force from a movable actuation element of a surgical instrument to the working parts moved by the actuation element, in particular to mouth parts of surgical forceps, by the fact that at least one wedge surface, belonging to the actuation element and rising perpendicular to its movement direction, is provided; and by a housing which can be spread apart by the wedge surface by movement thereof; and by the provision of an elastically spreadable ring circumferentially surrounding the housing in its spreading region.

The spreadable housing along with the elastically spreadable ring surrounding it are configured so that a specific force is necessary even to achieve a specific spreading. This force corresponds to the maximum force with which the mouth parts are to be acted upon. If forces which exceed this maximum force are then exerted on the actuation element in one direction, these forces cause a spreading of the housing. These forces are diverted from the actuation element via the wedge surface onto the housing, and utilized for reversible deformation (spreading). A relative movement thus takes place between housing and wedge surface.

The extent to which the housing is spread by the wedge surface is limited by the spreadable ring surrounding the housing in its spreading region. The geometrical configuration and the selection of the materials of the housing and spreadable ring, in combination with the inclination of the wedge surface, define the increase in load with displacement for the force limiting apparatus. This selection of parameters makes it possible, with an extremely slender design for the apparatus, to dissipate large forces into deformation if a threshold is exceeded. When the forces are no longer acting to excess, the elastic spreadable ring placed around the housing once again causes the housing to close, so that the wedge surface along with the actuation element is displaced back again. The apparatus thus operates not only as a dynamic force limiter, but also, because of the elasticity of the housing and the ring surrounding it in the spreading region, as a reversibly operating apparatus, so that following an overload situation the apparatus can be returned or reshaped into an initial position in which it is ready for the next overload situation.

Overloading of the mouth parts is thus prevented by the fact that forces which exceed the design load of the mouth parts are dynamically converted by the apparatus, i.e. are not passed on to the mouth parts. The mouth parts are thus loaded exclusively with forces at a magnitude for which they are designed and constructed, so that material fatigue, which can result in breakage, is largely prevented.

An apparatus of this kind for limiting the transfer of force to the mouth parts of a surgical instrument moreover has the advantage that the operator need not himself or herself take care that he or she does not exert too much force on the handle of the instrument, but rather can concentrate entirely on procedures in the operative area.

The object is completely achieved in this way.

In a preferred embodiment of the invention, the actuation element is displaceable axially along a shaft of the instrument, and the wedge surface extends in the axial direction of the actuation element.

The advantage of this embodiment is that the apparatus can easily be integrated into axially displaceable actuation elements which are implemented in the majority of surgical instruments that are used. The wedge surface provided according to the present invention extends in the axial direction and rises when viewed in the radial direction, so that the axial movement of the actuation element is converted into a radial spreading of the housing. This is easy to implement in design terms, for example by applying one or more wedges to the actuation element.

In a further embodiment of the invention, the angle of inclination α of the wedge surface lies in the range from approx. 8 degrees to 12 degrees.

The advantage of this feature is that the movement of the wedge surface relative to the housing proceeds harmoniously due to the low inclination of the wedge surface, and only a slight spreading of the housing takes place in the radial direction, so that no appreciable diametrical expansion occurs. As a result, the apparatus can be used even with instruments of very slender construction. This wedge angle range allows jam-free movement of the wedge surface along the inner side of the housing that is to be spread apart, both during spreading and as the wedge returns upon closing when no further overload forces are acting. A corresponding selection of the materials of the housing and the ring placed around it, in combination with this wedge surface angle range, allows a compact design, i.e. axial displacement movements of the wedge surface occur in the range from 1 to 3 mm, and the radial spreading movements caused thereby are in the range of fractions of a millimeter. This ensures at the same time that even extremely high overload forces caused by excessive squeezing are dissipated.

In a further embodiment of the invention, the wedge surface is configured as the outer surface of a cone.

It is advantageous in this context that the cone dissipates the forces onto the housing in uniformly circumferentially distributed fashion.

In a further embodiment of the invention, the housing has recesses extending in the movement direction of the actuation element and passing through the housing wall.

The housing is circumferentially segmented by the recesses. The advantage here is that the reversible spreadability of the housing is guaranteed in simple fashion, even if the housing itself is made of a poorly deformable material. The ends of the recesses determine the pivot points about which the segments are pivoted radially outward upon spreading.

In a further embodiment of the invention, each recess ends in a rounded expansion.

The advantage of this feature is that the notching forces acting on the material in the region of the end of the recesses during spreading of the housing wall segments placed circumferentially between the recesses are reduced, thus minimizing the stress concentrations in the regions which are exposed to continually increasing loads during spreading and closing. Material fatigue and thus cracking or notching of the housing wall are therefore prevented, even after numerous spreading and closing actions.

In a preferred embodiment of the invention, the housing has four recesses distributed uniformly about its circumference.

This has the advantage that four recesses can be produced with tolerable outlay in terms of production engineering, and that with slender instruments sufficient segmentation is present so that the housing can be manufactured from high-strength material, for example medical steel. It is understood that a larger number of recesses can also be provided, for example six or eight grooves.

In a further embodiment of the invention, the housing has circumferentially, in the region of the expansion, a trough-like depression which reduces the thickness of the wall of the housing.

The advantage of this feature is that the housing wall is relatively thin in the region of the trough-like depression, so that the spreading and closing movements of the housing segments are made possible in the manner of a film hinge.

In a further embodiment of the invention, the housing is made of plastic.

The advantage here is that the housing can be manufactured economically and designed as a replaceable part. Different plastics can be used in order to define the deformation properties of the housing and thus also the load increase with displacement for the apparatus according to the present invention.

In a preferred embodiment, the elastically spreadable ring has a slot.

The advantage of this feature is that the spreadability of the ring can be defined and predetermined for inherently very strong materials. Because of the geometry of the ring and the material selected for it, even a slight spreading movement can require very large forces, so that with particularly slender instruments no perceptible radial expansion occurs. Ideal linear spring characteristic curve conditions are present in such a small expansion range, so that precisely predefinable working conditions are present for the dynamic force limiter.

In a further embodiment of the invention, the ring can be attached at different axial positions on the housing.

This feature further enhances the variability of the apparatus, so that adjustments can be made to different overload situations simply by way of the axial placement position of the ring, the components otherwise being inherently identical.

In a further embodiment, the ring is received in an annular groove of the housing.

The advantage of this feature is that the ring is easily mounted and retained in lossproof fashion on the housing.

In a further embodiment of the invention, the ring is manufactured from metallic materials, in particular from steel, or from plastic material, in particular from fiber-reinforced plastics.

The advantage of this feature is that on the one hand it is possible to utilize materials suitable for medical purposes, which are suitable in terms of cleaning and sterilization capability and at the same time have the elastic properties which ensure a defined spreading and closing movement of the housing. Carbon-epoxy, Kevlar-epoxy, glass-epoxy, or similar plastics can be provided, for example, as the fiber-reinforced plastics.

In a further embodiment of the invention, the actuation element has a first segment which is immovably joined to the housing, and furthermore has a second segment which is separate from the first segment, the second segment carrying the wedge surface which is arranged inside the housing.

The advantage of this feature is that in an overload situation the second segment, which carries the wedge surface, causes the relative movement between actuation element and housing which results in the spreading movement, while the first segment, being immovably joined to the housing, remains unchanged. It is thereby possible, for example, to keep the mouth parts, joined immovably to the first segment, in a defined relative final position with respect to one another, so that even in an overload situation, i.e. during spreading, they do not move further. This is particularly advantageous if the mouth parts are already under a compressive or closing pressure against one another in this final position, and must not move further relative to one another in an overload situation.

In the permissible load range, nonpositive engagement exists between the two segments of the actuation element, so that, for example, the forceps with a force limiting apparatus has the same working behavior as a forceps without force limitation.

In an overload situation, the nonpositive engagement is interrupted in such a way that the maximum permissible load continues to be transferred via the actuation element, but the overload is diverted to other components. The particular property of the force limiter according to the present invention is that after the overload situation is terminated, the unrestricted nonpositive engagement between the two segments is restored by automatic return, and the forceps, for example, is once again unrestrictedly ready for use. The force limiter thus acts as a "dynamic force limiter" which reacts to individual overload situations during use without impairing the functionality of the surgical instrument.

In a further embodiment of the invention, in a normal load operating position the first segment rests against the second segment, and in the overload operating position the second segment has detached from the first segment.

The fact that the two segments rest against one another allows movements directed back and forth to be transferred with zero clearance via the actuation element; only in an overload situation does the second segment detach from the first segment.

The threshold value corresponds to the force necessary so that the unrestricted nonpositive engagement between the two segments of the actuation element just ceases to exist, and so that force components begin, by way of the apparatus, to be diverted to other constituents of the apparatus. This is accomplished by the fact that the forces which are exerted on the actuation element in one direction and exceed the threshold value result in spreading of the housing.

In a further embodiment of the invention, the first segment of the actuation element is immovably joined to the housing via a threaded connection, the depth to which it is threaded in allowing an adjustment of the design point of the apparatus.

This feature has the considerable advantage that a specific design point can be set during assembly. As it is threaded in, the end of the first segment encounters the correspondingly opposing end of the second segment which carries the wedge surface or cone. Further threading into the housing then already causes a certain displacement of the wedge surface, which is then immediately displaced in the spreading direction, this spreading being resisted by the counterforce of the outer ring. Only a force which is sufficient to move the wedge surface farther will cause spreading of the housing, i.e. a movement beyond the design point. For a single instrument that, for example, is operated with different mouth parts, it is thereby possible to set an optimum design point for the application.

In a further embodiment of the invention, the housing is immovably joined to the handle, the actuation element carrying the wedge surface which is arranged inside the housing.

The advantage of this feature is that via the continuous actuation element, a direct nonpositive engagement always exists between the handle and the mouth parts that are to be moved, as is necessary, for example, in scissors; an increase in the hand force on the handle is always converted into an additional displacement and, depending on the design and/or preadjustment of the apparatus, into increasing spreading of the housing and ring. Force limitation is accomplished by the fact that at the maximum applicable hand force, the spreading is limited by the material properties and configuration of the housing and ring.

In a surgical instrument that is equipped with an apparatus according to the present invention, it is preferred that the apparatus be arranged in the proximal region of the handle.

This feature has the advantage that the apparatus can be arranged in integrated and thus also protected fashion in the region of the handle at the proximal end of the shaft, so that in the region of the shaft and the mouth parts as such, there is no diametrical enlargement at all due to the additional installation of the apparatus.

It is understood that the features mentioned above and those yet to be explained below can be used not only in the respective combinations indicated, but also in other combinations or in isolation, without leaving the context of the present invention.

BRIEF DESCRIPTION OF THE DRAWING

The invention will be explained and described in more detail below with reference to a selected exemplifying embodiment in conjunction with the appended drawings, in which.

DETAILED DESCRIPTION OF A PREFERRED EMBODIMENT

Figure 1:
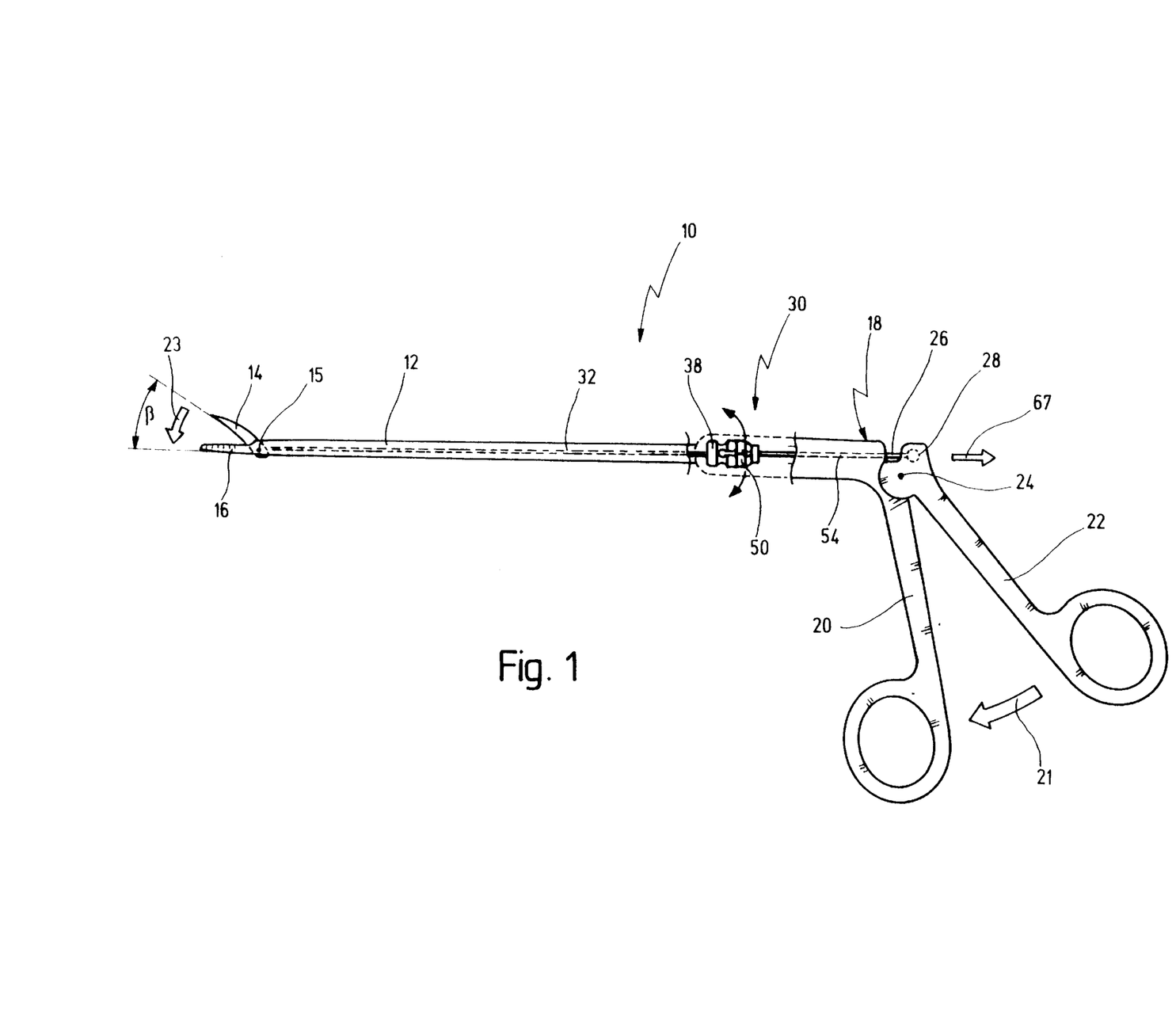
FIG. 1 shows a side view of a surgical instrument in the form of a forceps, in which an apparatus according to the present invention for limiting the transfer of force is installed.

FIG. 1 shows a surgical instrument in the form of a grasping and dissection forceps, designated in its entirety with the reference number 10.

Forceps 10 has an elongated tubular shaft 12 at whose distal end two mouth parts 14 and 16 are arranged.

Mouth part 16 is rigidly joined to shaft 12, and mouth part 14 is arranged pivotably about an axis 15.

A handle 18 is arranged at the proximal end of shaft 12.

Handle 18 has a stationary handle element 20 that is joined immovably to shaft 12. A movable handle element 22 is arranged, pivotably about a hinge axis 24, on stationary handle element 20.

A rod-shaped actuation element 26, which is joined at the distal end to movable mouth part 14 at a slight distance from its pivot axis 15, is arranged so as to pass through shaft 12. At the proximal end, actuation element 26 extends out beyond stationary handle element 20 and is received in a ball-and-socket joint 28 of movable handle element 22. In FIG. 1 mouth parts 14 and 16 are open and thus enclose an opening angle β. The maximum opening angle is usually 50 degrees.

When forceps 10 is grasped in this position, with two fingers of one hand engaging into the end-mounted finger loops of handle elements 20 and 22, and when movable handle element 22 is moved toward stationary handle element 20, as indicated in FIG. 1 by an arrow 21, actuation element 26 is displaced in the proximal direction as indicated by an arrow 67. This linear displacement movement of actuation element 26 is converted into a closing movement of the mouth parts, i.e. movable mouth part 14 is pivoted toward immovable mouth part 16, as indicated in FIG. 1 by an arrow 23.

It is also evident from FIG. 1 that the distance from the finger loop to hinge axis 24 is substantially greater than the distance from hinge axis 24 to ball-and-socket joint 28. The force applied to movable handle element 22 by a finger inserted into the finger loop is thus amplified by the lever effect; usual ratios are 10:1. If the force acting on movable handle element 22 is approximately 10 kp, this is amplified by a factor of 10, i.e. to 100 kp. Surgical instruments of this kind are usually designed for such forces. It is possible, however, for one hand to exert substantially greater forces, which are in the range of 15 kp or more and are then correspondingly amplified tenfold by the lever effect.

An apparatus 30 for limiting the transfer of force is provided so that these excessive forces are not diverted onto mouth parts 14 and 16.

As is evident from FIG. 1, the apparatus is arranged at the distal end of stationary handle element 20, from the end of which shaft 12 protrudes.

Figure 2:
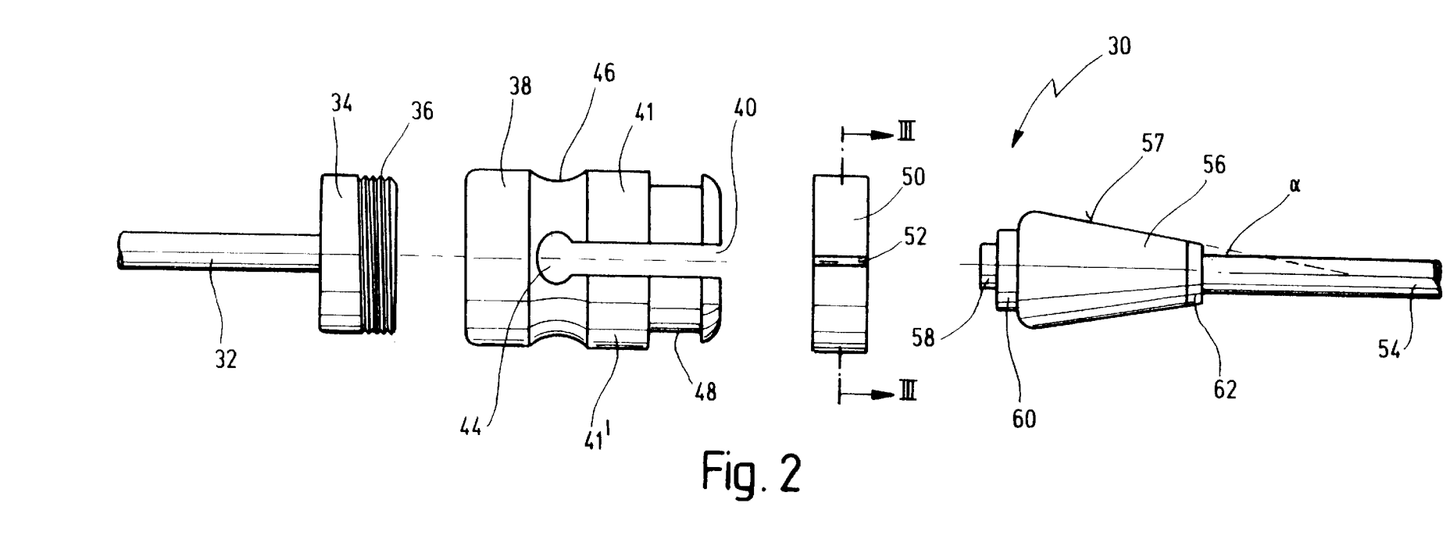
FIG. 2 shows, at greatly enlarged scale, an exploded view of the apparatus shown in FIG. 1.

As shown in FIGS. 1 and 2, apparatus 30 is connected distally to a first segment 32 of the rod-shaped actuation element 26.

For this purpose, a screw 34 with external threads 36 is provided at the proximal end of said segment 32.

Screw 34 is provided in order to be threaded into corresponding internal threads 37 at the distal end of a roughly hollow-cylindrically shaped housing 38.

Four axially extending recesses 40 are cut, in circumferentially uniformly distributed fashion, into wall 42 of housing 38. Each recess 40 passes completely through wall 42 in the radial direction, opens in the proximal direction, and extends over approximately two-thirds of the axial length of housing 38.

Each recess 40 ends in an approximately circular expansion 44.

Viewed in the circumferential direction, each two adjacent recesses 40 then have corresponding segments 41, 41', etc. of wall 42 of housing 38 lying between them.

Figure 4:
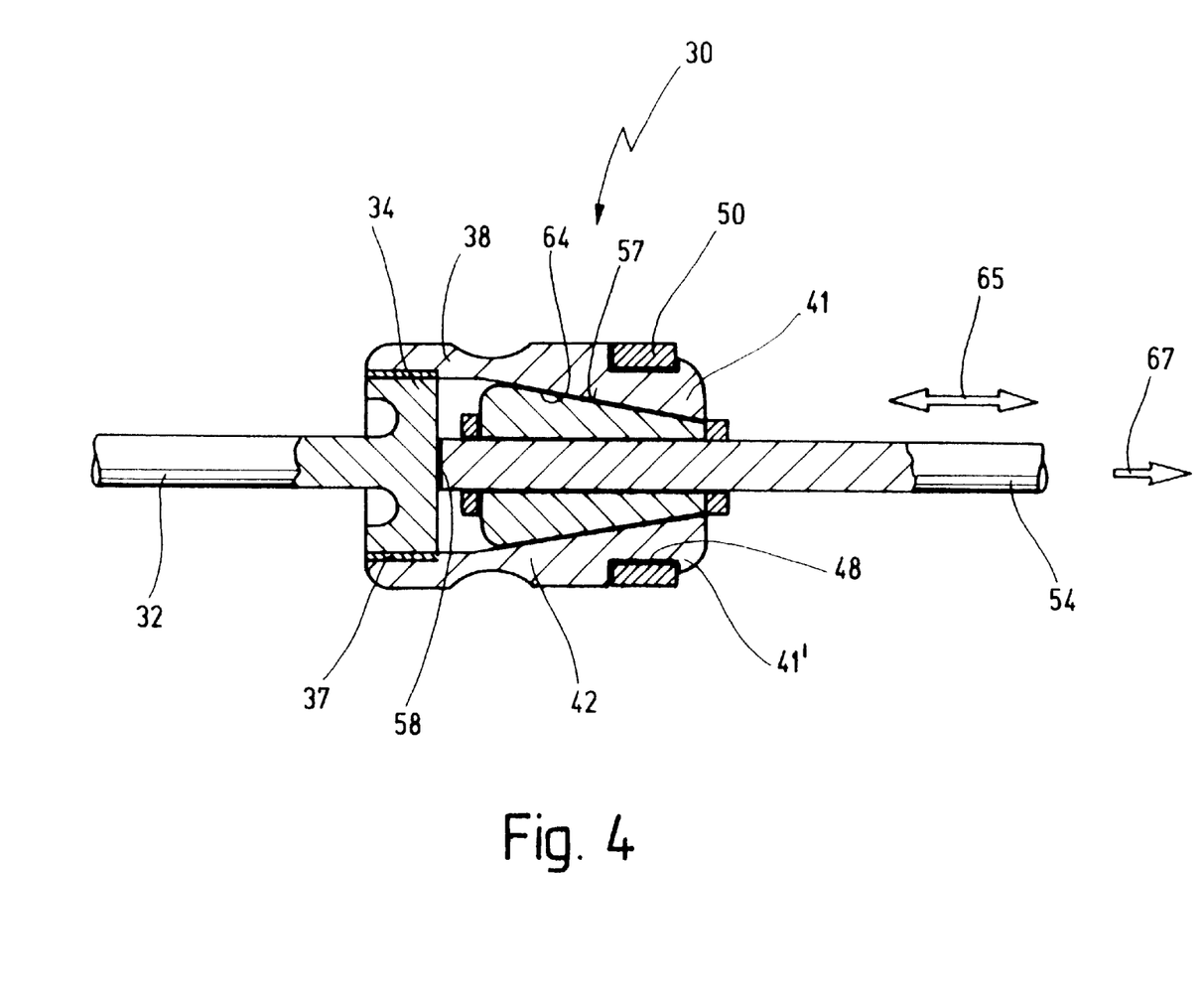
FIG. 4 shows a partial longitudinal section through the apparatus in the assembled state, in a first operating position.

An annular depression 46 is cut out from the exterior of housing 38 in the region of expansion 44 of recess 40, so that the thickness of wall 42 is reduced in this region, as is apparent in particular from the sectioned representation of FIG. 4.

A circumferential annular groove 48 whose cross section is approximately rectangular is recessed in the region of the proximal end of housing 38.

Annular groove 48 serves to receive a ring 50.

Figure 3:
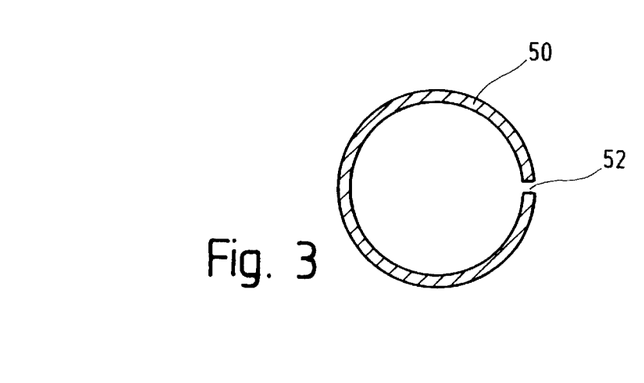
FIG. 3 shows a section along line III—III in FIG. 2.

It is apparent from the sectioned representation of FIG. 3 that the ring is equipped with a slot 52.

A cone 56 is mounted on a second segment 54 of actuation element 26. Cone 56 has a conical wedge surface 57 which rises from proximal to distal at a wedge angle a of approximately 10 degrees. Cone 56 is attached to segment 54 by way of two attachment rings 60 and 62. The location is such that one end 58 of segment 54 projects distally from cone 56.

A corresponding internal cone 64 is provided on the inner side of wall 42 of housing 38, as is evident in particular from FIG. 4.

The individual parts shown in FIG. 3 are mounted so that slotted ring 52 is slid over the proximal end of housing 38 until it snaps into annular groove 48. Second segment 54, with cone 56 mounted on it, is then inserted into housing 38 from the distal end until its wedge surface 57 is resting against internal cone 64.

Screw 34 is then threaded into internal threads 37 until the end surface of screw 34 comes to rest against end 58, as shown in FIG. 4. In this position cone 56 is resting against internal cone 64.

The assembly can be moved back and forth within a specific force range, as indicated in FIG. 4 by an arrow 65, without causing displacement of the components of the apparatus relative to one another.

Figure 5:
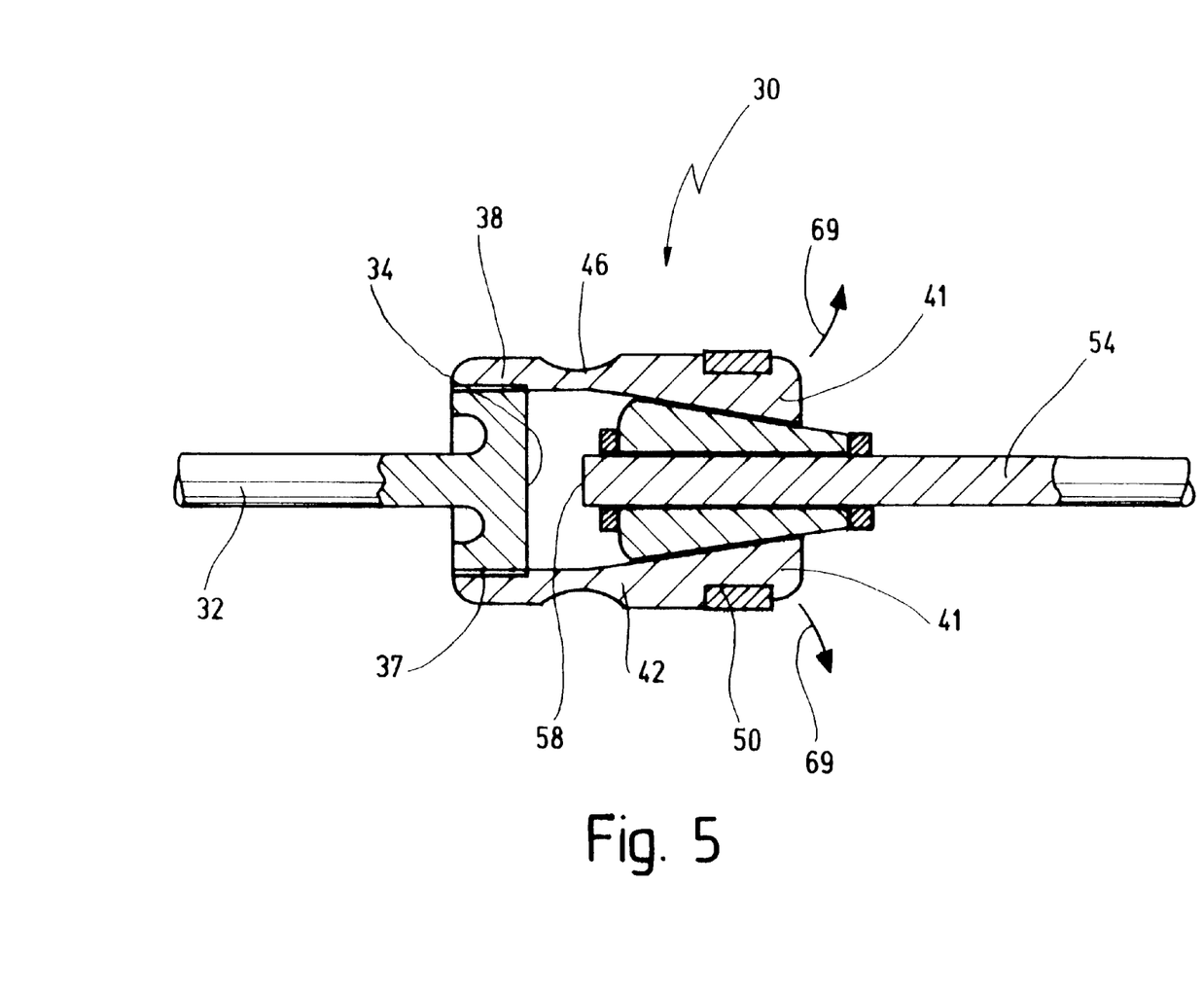
FIG. 5 shows a representation comparable to the representation of FIG. 4, in a second operating position in an overload situation.

For example, if the movement indicated in FIG. 1 by arrow 21 is performed, the entire assembly made up of the two segments 32 and 54 of actuation element 26, housing 38, ring 50, and cone 56 moves in the proximal direction, for example, until mouth parts 14 and 16 enclose an angle of only 20 degrees. This is an angle at which, for example, a grasping forceps holds a piece of tissue or a surgical element, whether a muslin sponge or a needle, between mouth parts 14, 16. Further closure of the mouth parts beyond the design point of the apparatus requires application of a substantially greater force. Apparatus 30 then ensures that this force is not transferred to mouth parts 14 and 16, but rather that the force is converted in defined fashion into deformation work. This conversion is accomplished by the fact that if these excessive forces act on second segment 54, as shown in FIG. 4 by an arrow 67, cone 56 moves in the proximal direction relative to housing 38, and the four segments 41, 41', . . . of the slotted wall 42 are spread radially, as shown in FIG. 5 by arrows 69.

The area of thinned material, similar to a film hinge, in the region of depression 46 promotes the defined pivot movement.

The radial spreading displacement is limited by ring 50; in other words, the predominant portion of the excess force is diverted into spreading of ring 50. As is evident from the representation of FIG. 5, end 58 of second segment 54 has lifted away from first segment 32. The displacement travel in FIG. 5 is shown in exaggerated fashion for illustrative purposes; the stroke length lies in the range from 1 to 3 mm.

When the excessive force is no longer acting on second segment 54, ring 50 once again, because of its elasticity, presses the housing and segments 41, 41', . . . radially inward. As a result, cone 56 is once again displaced in the distal direction until its end 58 strikes against the end surface of screw 34 of the first segment.

It is evident from the description above that the spring characteristic curve of apparatus 30 according to the invention for limiting the transfer of force is defined by three essential parameters, namely:

the construction of housing 38, i.e. the material selection, geometry, number of recesses 40, and the geometry of annular depression 46;

the cone angle $\alpha$, which lies in the range from approximately 8 to 12 degrees; and the design of ring 15, i.e. the material, shape (thickness and width), and whether or not a slot 52 is provided. A slot 52 is always provided in the case of metallic ring materials; with particularly elastic plastic materials, a completely closed ring can also be provided.

Figure 6:
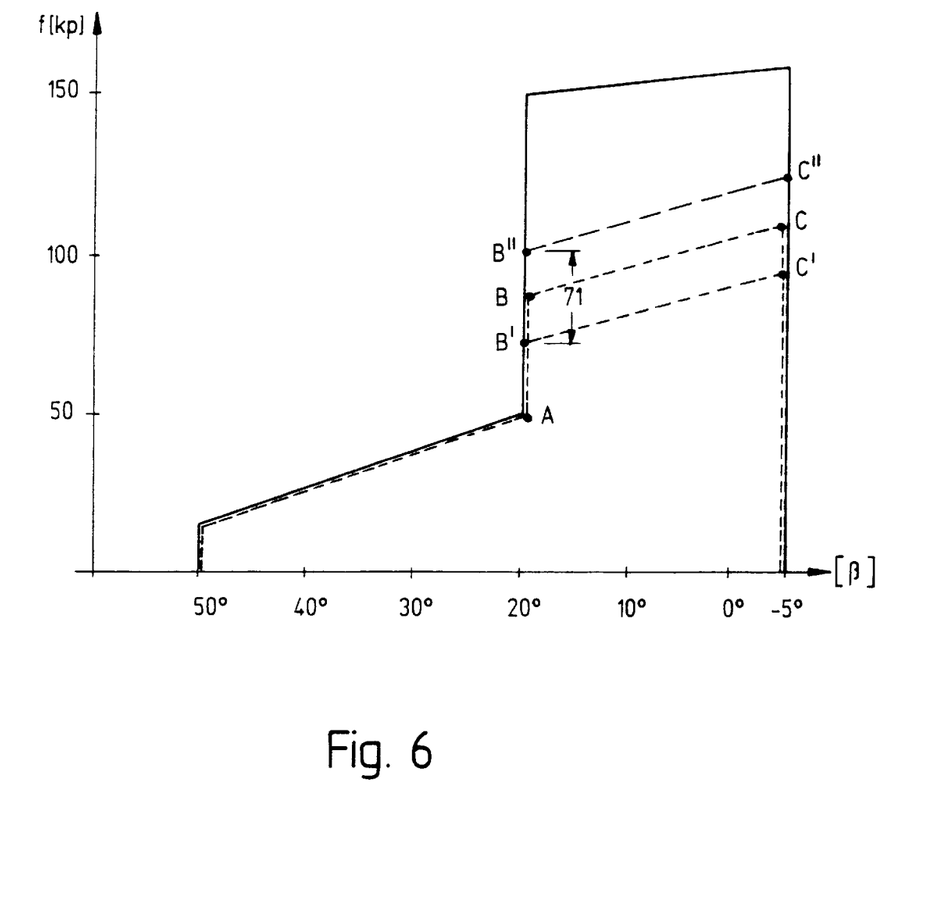
FIG. 6 shows a schematic force-displacement diagram for the apparatus according to the present invention.

FIG. 6 depicts a typical force-displacement diagram for the mouth parts of a forceps, the object in this case being firmly grasped at an opening angle of approximately 20 degrees. The solid line depicts the diagram for a forceps according to the existing art with no force limitation.

It is evident from the enveloping curve (force envelope) that beginning at a maximum opening angle of 50 degrees, there is a gentle linear rise up to the desired closing angle of 20 degrees. An increase in the applied force up to approximately 150 kp then results in further closing, with deformation, to beyond a closing angle of 0 degrees.

The dashed lines in the diagram of FIG. 6 depict the corresponding enveloping curve with an apparatus 30 according to the present invention (dynamic force limiter).

Point A represents the starting point after which mouth parts 14 and 16 are adjusted up to a desired closing angle of approximately 20 degrees, and the object received by the forceps is grasped firmly and acted upon by increasing holding force.

The location of point A depends on the physical properties of the object received by the forceps.

Point B represents the design point of the force limiter, i.e. the point at which reversible deformation begins when a specific force (in this case approximately 90 kp) is exceeded. Greater applied forces are now no longer conveyed onto mouth parts 14 and 16, but rather utilized to deform housing 38 and ring 50.

A double arrow 72 indicates that by varying the components of apparatus 30, it is possible in principle to freely select a certain design range (here B' to B").

Point C represents the limit load point of the force limiter. Point C changes with the changes in design point B as shown in FIG. 6.

It is clearly evident, from the profile of the enveloping curve (dashed line) in the presence of the force delimiter as compared to the enveloping curve (solid line) without the force delimiter, that the forces applied beyond the design point are effectively converted by the force delimiter and are not transferred to the mouth parts.

Fine adjustment of the design point can be accomplished by rotating screw 34 of first segment 32, i.e. once the end surface of screw 34 has arrived at end 58, cone 56 can already be displaced somewhat in the spreading direction by screwing in further, thus raising the setting of point B.

A different setting of design point B can be achieved by way of the parameters described above:

Construction of housing 38

Cone angle $\alpha$

Design of ring 15.

What is claimed is:

1. Surgical instrument comprising
   a movable actuation element;
   at least one working part moved by said actuation element,
   an apparatus for limiting a transfer of a force transferred via said actuation element to said at least one working part, said apparatus having at least one wedge surface associated to said actuation element, said wedge surface rising perpendicular to its movement when moving said actuation element;
   a housing which can be spread apart by said wedge surface by movement thereof, thereby deforming said housing to a spread housing; and
   an elastically spreadable ring circumferentially surrounding said housing in its spreading section, said elastically spreadable ring being spread by said housing when it is spread apart by said wedge surface, and said ring can close said spread housing when said wedge surface is moved out of its spreading engagement with said housing.

2. The surgical instrument of claim 1, wherein said actuation element is displaceable axially along a shaft of said instrument, and wherein said wedge surface extends in an axial direction of said actuation element.

3. The surgical instrument of claim 1, wherein an angle of inclination $\alpha$ of said wedge surface lies in a range from approx. 8 degrees to 12 degrees.

4. The surgical instrument of claim 1, wherein said wedge surface is configured as an outer surface of a cone.

5. The surgical instrument of claim 1, wherein said housing has recesses extending in a movement direction of said actuation element and passing through a wall of said housing.

6. The surgical instrument of claim 5, wherein each recess ends in a rounded expansion.

7. The surgical instrument of claim 6, wherein said housing has four recesses distributed uniformly about its circumference.

8. The surgical instrument of claim 1, wherein said housing has a trough-like depression extending circumferentially in a region of expansion of said housing, which said trough-like depression reduces a thickness of a wall of said housing.

9. The surgical instrument of claim 1, wherein said housing is made from a metallic material.

10. The surgical instrument of claim 9, wherein said housing is made from medical steel.

11. The surgical instrument of claim 1, wherein said housing is made from a plastic material.

12. The surgical instrument of claim 1, wherein said elastically spreadable ring has a slot.

13. The surgical instrument of claim 1, wherein said ring can be attached at different axial positions on said housing.

14. The surgical instrument of claim 1, wherein said ring is received in an annular groove of said housing.

15. The surgical instrument of claim 1, wherein said ring is manufactured from metallic material.

16. The surgical instrument of claim 15, wherein said ring is made from steel.

17. The surgical instrument of claim 1, wherein said ring is made from plastic material.

18. The surgical instrument of claim 1, wherein said actuation element has a first segment which is immovably joined to said housing, and furthermore has a second segment which is separate from said first segment, said second segment carrying said wedge surface which is arranged inside said housing.

19. The surgical instrument of claim 18, wherein in a normal load operating position said first segment rests against said second segment, and in an overload operating position said second segment has detached from said first segment.

20. The surgical instrument of claim 19, wherein said first segment is immovably joined to said housing via a threaded connection, the depth to which it is threaded in allowing an adjustment of a design point of said apparatus.

21. The surgical instrument of claim 1, wherein said housing is immovably joined to a handle, said actuation element carrying said wedge surface is arranged inside said housing.

22. The surgical instrument of claim 1, wherein a scissor-like handle is provided at a proximal end of a shaft, said at least one working part comprises one movable mouth part movable via said actuation element, said movable mouth part is provided at a distal end of said shaft.

23. The surgical instrument of claim 1, wherein said apparatus is arranged near said handle.

24. Surgical instrument comprising:

a shaft extending along an axis;

a movable actuation element axially displaceable along said shaft;

at least one working part moved by said actuation element;

an apparatus for limiting a transfer of a force transferred via said actuation element to said at least one working part, said apparatus having at least one wedge surface associated to said actuation element and extending in an axial direction, said wedge surface rising perpendicular to its movement when moving said actuation element;

a housing which can be spread apart by said wedge surface by movement thereof, and an elastically spreadable ring circumferentially surrounding said housing in its spreading section, said elastically spreadable ring can close said housing when said wedge surface is moved out of its spreading engagement with said housing.

* * * * *

UNITED STATES PATENT AND TRADEMARK OFFICE
CERTIFICATE OF CORRECTION

PATENT NO. : 6,096,058
DATED : August 1, 2000
INVENTOR(S) : Hartmut Boche

It is certified that error appears in the above-indentified patent and that said Letters Patent is hereby corrected as shown below:

Title page, item [30], should read --

Foreign Application Priority Data

July 22, 1997 [DE] Germany 197 31 453 --

Signed and Sealed this

Tenth Day of April, 2001

Attest:

NICHOLAS P. GODICI

Attesting Officer     *Acting Director of the United States Patent and Trademark Office*